US009566425B2

(12) United States Patent
Meisberger et al.

(10) Patent No.: US 9,566,425 B2
(45) Date of Patent: Feb. 14, 2017

(54) LINE, IN PARTICULAR A LINE OF A BLOOD TUBING SYSTEM OR OF A BLOOD BAG SYSTEM

(75) Inventors: Artur Meisberger, St. Wendel (DE); Alexandra Huber, Dreieich (DE)

(73) Assignee: PRESENIUS HEMOCARE GMBH, Bad Homburg (DE)

( * ) Notice: Subject to any disclaimer, the term of this patent is extended or adjusted under 35 U.S.C. 154(b) by 1273 days.

(21) Appl. No.: 11/919,330

(22) PCT Filed: Apr. 27, 2006

(86) PCT No.: PCT/EP2006/003937
§ 371 (c)(1),
(2), (4) Date: Mar. 26, 2009

(87) PCT Pub. No.: WO2006/114319
PCT Pub. Date: Nov. 2, 2006

(65) Prior Publication Data
US 2009/0227961 A1    Sep. 10, 2009

(30) Foreign Application Priority Data

Apr. 28, 2005  (DE) .......................... 10 2005 019 855

(51) Int. Cl.
*A61M 39/08*   (2006.01)
*A61M 39/22*   (2006.01)

(52) U.S. Cl.
CPC ........... *A61M 39/08* (2013.01); *A61M 39/221* (2013.01)

(58) Field of Classification Search
CPC ...... A61M 39/08; A61M 39/221; F16K 11/00; F16K 7/00
USPC ....... 604/250, 246, 252, 256, 112, 403, 412, 604/905, 96.01, 102.01, 34; 134/67
See application file for complete search history.

(56) References Cited

U.S. PATENT DOCUMENTS

| 4,181,140 A * | 1/1980 | Bayham et al. ........... 137/68.28 |
| 4,913,401 A | 4/1990 | Handke |
| 5,071,411 A | 12/1991 | Hillstead |
| 5,188,629 A * | 2/1993 | Shimoda ........................ 604/412 |
| 5,265,847 A * | 11/1993 | Vorhis .......................... 251/342 |
| 6,132,413 A | 10/2000 | Mathias et al. |
| 2004/0220542 A1* | 11/2004 | Cise et al. ..................... 604/500 |
| 2006/0015074 A1* | 1/2006 | Lynn ............................. 604/250 |

FOREIGN PATENT DOCUMENTS

DE    8 701 154 U1    3/1987
FR    1 129 284    1/1957

* cited by examiner

*Primary Examiner* — Bhisma Mehta
*Assistant Examiner* — Brandy S Lee
(74) *Attorney, Agent, or Firm* — Jacobson Holman, PLLC.

(57) ABSTRACT

A line, in particular to a line of a blood tubing system or of a blood bag system, having a closing member blocking the line passage, with the closing member being formed by a plastically deformable closing body which is arranged in the line and which closes the line in at least one state and with at least the portion of the line in which the closing body is located being made flexible.

24 Claims, 9 Drawing Sheets

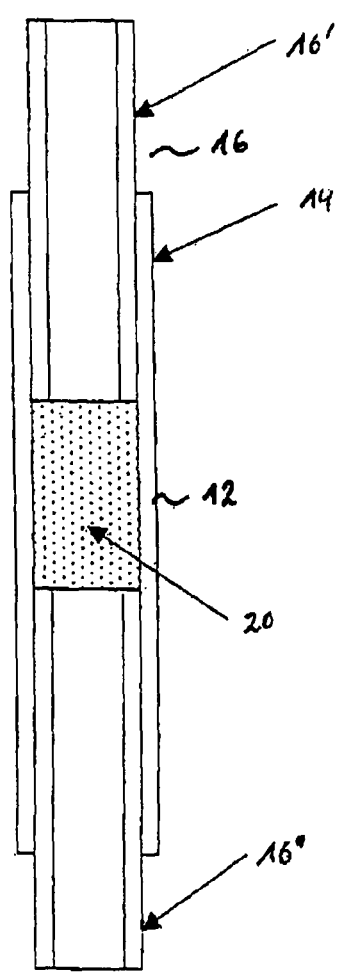
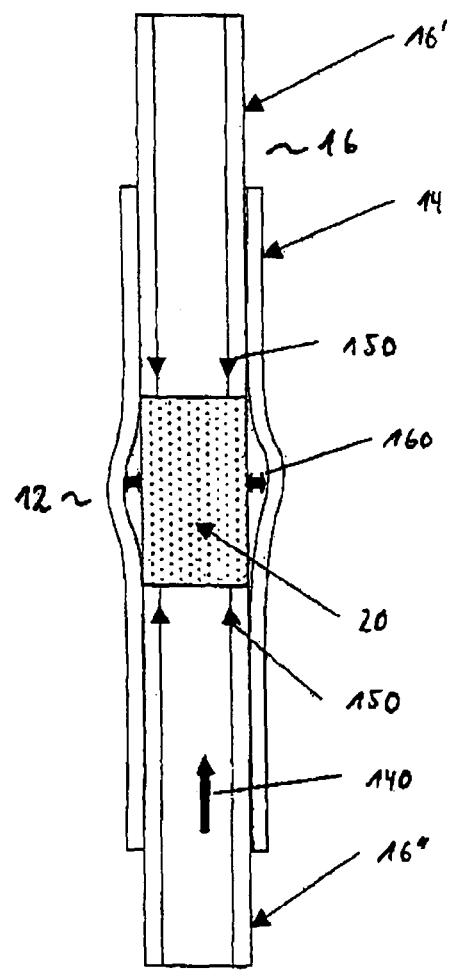

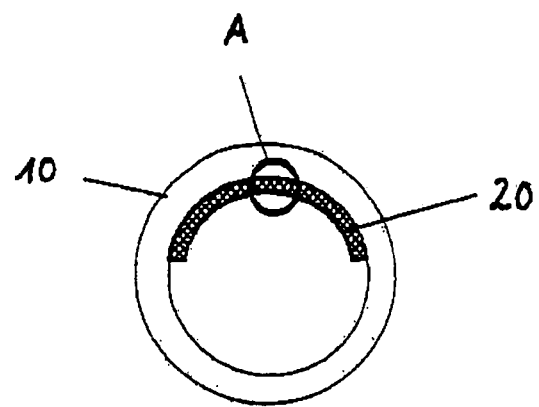
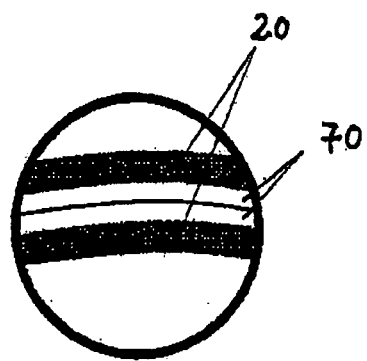
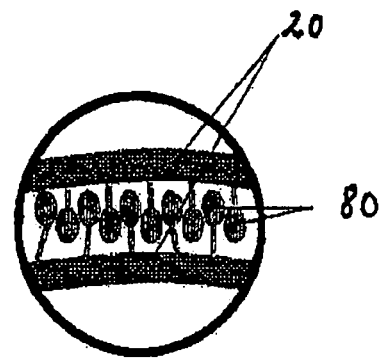
Fig. 15

LINE, IN PARTICULAR A LINE OF A BLOOD TUBING SYSTEM OR OF A BLOOD BAG SYSTEM

This is a national stage of PCT/EP2006/003937 filed Apr. 27, 2006.

BACKGROUND OF THE INVENTION

1. Field of the Invention

The invention relates to a line, in particular to a line of a blood tubing system or of a blood bag system having a closing member blocking the line passage.

2. Description of the Related Art

It is known with blood tubing systems and blood bag systems known today to provide a closure which can be opened from the outside, which remains sterile and which is opened by breaking a plastic part. After the breaking of the so-called break cone, a passage for the previously enclosed or blocked liquid is released. A blood bag is known from U.S. Pat. No. 6,132,413 having a line which is closed by such a breakable member. To open the line passage, the line with the member therein is bent, which has the result that the member breaks and in so doing releases the line passage. A disadvantage of the closure known from the prior art comprises the fact that only a comparatively small cross-section is released for the flowing medium. In addition, particles arise due to the breaking off of plastic parts and said particles can enter into the organism of a patient. It is furthermore disadvantageous that sharp burrs can occur at the plastic which can cause hemolysis when blood flows through. It must finally be named as a further disadvantage that the manual breaking of the cones can cause pain for the personnel on frequent repetition of this action.

SUMMARY OF THE INVENTION

It is the object of the invention to further develop a line of the initially named kind such that its closing member can be opened such that a comparatively large cross-section is released for the flowing medium and such that furthermore the disadvantages known from the prior art of the arising of particles and of sharp burrs no longer occur. It should furthermore be made possible for the closing member also to be able to be opened by a machine.

This object is solved by a line, in particular a line of a blood tubing system or of a blood bag system, having a closing member blocking the line passage. Provision is accordingly made for a plastically deformable closing body to be arranged in the line which closes the line in at least one state and for at least the portion of the line in which the closing body is located to be made flexible.

The term "line" is to be understood with a wide meaning and includes any desired region which is flowed through such as line portions, tubes as well as connector regions of e.g. blood bag systems.

In the non-deformed state, the closing body blocks the line such that the passage for media is blocked. To open the passage, the closing body is deformed from the outside such that a flow of medium is possible. In this connection, the line surrounding the closing body must be so flexible that the deformation of the closing body is possible and subsequently a region is released for the flow of the medium. This can take place by restoring forces of the line itself or by outside support.

The closing body can be made as solid, as porous or as a hollow body which is made open or closed on one or more sides. If the plastically deformable closing body is made as a hollow body, the remaining volume of the closing body is so low after its deformation that a substantially unimpeded passage is ensured for the medium.

The closing body can be made in accordance with the invention such that no sharp burrs arise after its deformation which can cause damage to the blood and such that also no particles arise during the deformation which could enter into the patient's blood.

Since only a simple squeezing movement is required to open the closure, the present invention is particularly suitable for the processing or opening of the line by a machine. A manual opening is naturally likewise conceivable which is comfortable and ergonomically possible for the user.

The core of the invention comprises the fact that the closing body is brought from a shape in which it closes the line into a shape which permanently releases the passage through the line by the effect of force.

The closing body can be solid, it can be hollow, open or closed; it can also comprise porous material or also be hollow and have a filling.

In a conceivable embodiment, the closing body is filled with a liquid, preferably with a liquid compatible for the patient such as with a saline solution. Provision can be made in this connection for the liquid to be accommodated in a wrapping, for example a bag, which bursts when pressure is applied, for example by the hand, and releases the liquid.

To ensure good adhesion between the closing body, on the one hand, and the flexible line, on the other hand, provision can be made for the closing body and the portion of the line in which the closing body is located to be made of materials or comprise materials which adhere to one another. It can thereby be ensured that the line remains sealed up to a comparatively high internal pressure.

Additional possibilities of increasing the internal pressure which can be tolerated comprise the design of the surface property of the closing body and inner side of the wall of the flexible line, which can be porous or rough, for example, whereby the adhesion of the closing body to the line is improved.

The adhesion between the closing body and the line can be improved additionally or alternatively by materials which connect the closing body to the line, such as glue, for example.

In a further embodiment of the invention, provision is made for the line to have a first line part and a second line part which are in fluid-tight communication with one another at least one connection point, with the closing body closing the second line part in at least one state and with the first and second line parts being arranged at least portion-wise in that region of the second line part in which the closing body is located such that the first line part surrounds the second line part and both line parts are spaced apart from one another or can be released from one another in this region.

Such an embodiment of the line is in particular of advantage when high demands are made on the pressure resistance of the closure of the line. It is, for example, conceivable, that a ring-shaped peripheral space is present or arises on exertion of pressure between the first and second lines, which can both be made flexible, with a corresponding pressure prevailing in said space on the exertion of pressure onto the first line. This has the result that the second, inwardly disposed line, is pressed onto the closing body. An opening of the closure independently of the internal pressure is thereby completely prevented.

It can be determined by the positioning of the closing body with respect to the peripheral connection of the first and second line parts whether the pressure resistance is given by one side or by both sides of the closing body.

The lines, which are at least flexible in the region of the closing body, can also be components of an injection molded part or can be lines made in a different process.

It is particularly preferred when the first and second line parts are arranged concentrically with respect to one another.

Provision is made in a further embodiment of the invention that, in that portion in which the closing body is arranged in the second line part, both line parts are spaced apart from one another and that, in a region adjacent thereto, both line parts are connected to one another by means of a connection portion which extends conically, for example.

Provision is made in a further embodiment of the invention that the second line part is accommodated in the first line part and that the connection position in the marginal region of the second line part, or spaced apart therefrom, is, for example, arranged in a central region of the second line part. The closing body can likewise be accommodated centrally in the second line part.

The middle region of the closing body can be at the level of the connection point.

Provision can furthermore be made that the second line part is arranged partially in the first line part and partly projects therefrom, with the connection point being arranged in the end region of the first line part.

In a further embodiment of the invention, an adapter is provided which is plugged onto the first and second line parts. It is conceivable that the line parts have a connection point independently of the adapter and that the adapter is e.g. adhesively bonded onto the end portion of the line parts. It is furthermore conceivable that the adapter presses the line parts in a fluid-tight manner with one another to form the connection point. Provision is made in a possible embodiment that the first and second line parts terminate with one another and that the adapter is placed onto the end faces of the line ends. A further line portion can be provided in the other end region.

A first line part and a second line part are provided in a further embodiment of the invention, with the second line part being made in two parts and each of the parts terminating in a blunt manner at the closing body, with the first line part surrounding the second line part and being in fluid-tight communication with the parts of the second line part at both sides of the closing body. The region between the parts of the second line part and the closing body is hot made fluid tight, but medium can rather flow through it. This throughflow takes place on that side of the closing body on which pressure is exerted. The medium providing the pressure and located in the second line part flows through the region between the end face of the second line part and the adjacent end face of the closing body and enters in this manner into that region of the first line part which surrounds the closing body. This has the result that the first line part undergoes a bulging action and thereby becomes shorter in the longitudinal direction. This in turn has the result that the parts of the second line part are pressed at their end faces onto the closing body so that a reliable sealing is created.

The term of the "plastically deformable closing body" or of the "plastic deformation of the closing body" is not only to be understood as the case that the closing body is made plastic, but also the case that the closing body is made resiliently and that means are provided which fix the flexible or resilient closing body in a deformed position in which it at least partly releases the line passage. If the closing body is made of flexible material and if the system pressure enters into the interior of the flexile closing body, as is e.g. the case with a piece of flexible line closed at one side, the closing body can expand under pressure with the flexible line surrounding it, whereby the closure remains sealed. So that the closing body does not return to its original shape, which closes the line, after its deformation, the flexible closing body must be held in that position in which it at least party releases the line passage. It is, for example, conceivable for this purpose for the flexible or resilient body to be combined with plastic materials.

Any other means can also be used with which the restoration of the deformed resilient closing body into its closing position is prevented. It is e.g. conceivable that glue is provided for this purpose. This can e.g. fix regions of the closing body adjacent to one another in this position in the deformed state. It is e.g. possible that the closing body is made hollow and has an adhesive layer on its inner side.

Furthermore a hook and loop fastener can be provided as the means fixing the closing body in its deformed position. It can, for example, be arranged on the inner side of a closing member made as a hollow body and can ensure in the deformed state that the adjacent walls of the closing body are fixed to one another. It is generally also conceivable that a part of the hook and loop fastener is arranged at the line and the complementary part of the hook and loop fastener is arranged at the closing body.

The present invention furthermore relates to a method of opening a line, with the closing body being plastically deformed from that state in which it closes the line for the purpose of opening the line such that a passage through the line is released. The deformation preferably takes place from the outside, i.e. through the line.

The deformation of the closing body for the purpose of releasing the passage can be carried out, for example, by means of a tool. An advantage of the invention comprises the fact that not only a manual actuation is possible, but also an actuation by a machine. The tool can thus be a component of a machine or apparatus for the opening of the line. The use of hand-actuated pincers is also conceivable.

The tool can be a tool with smooth jaws. It is likewise conceivable that the tool has one jaw with a projection and one jaw with a recess into which the projection engages when the tool is closed.

A deformation of the closing body preferably takes place such that it is fixed against displacement in the line after its deformation. Such an embodiment of the invention makes the use of special holding or fixing members superfluous which prevent a displacement of the closing body after its deformation. Embodiments of the invention are naturally also conceivable in which such fixing means are provided.

The invention furthermore relates to a blood tube or to a blood bag having a line in accordance with the invention.

Metals such as aluminum or plastics such as polyethylene can be considered as materials for the closing body, for example. The plastic can then be made brittle and can be comminuted into individual parts on its deformation.

If the line should be used in the medical field, provision is preferably made that the closing body is blood-compatible or has a blood-compatible coating.

The introduction of the closing body into the line can take place, for example, in that the closing body is mechanically inserted into the line. To ensure a good fit and a good seal, the external dimensions of the closing body should be slightly above the internal dimensions of the line so that the line is slightly extended on insertion and the closing body remains at the desired position and is sealingly accommodated in the line.

It is also conceivable to shrink the line at least in that region in which the closing body is located after the introduction of the closing body into the line. The line can thus also be shrunk onto the closing body. The process of shrinking advantageously takes place under the effect of heat. It is conceivable that the shrinking takes place during the heat sterilization. It is equally naturally possible to carry out the procedure of shrinking independently of the heat sterilization.

BRIEF DESCRIPTION OF THE DRAWINGS

Further details and advantages of the invention will be explained in more detail with reference to an embodiment shown in the drawing. There are shown:

FIGS. 13, 14: schematic representations of the line having a first line part and a second line part which is made in two parts in an embodiment pressure tight on two sides before the exertion of pressure (FIG. 13) and after the exertion of pressure (FIG. 14); and FIG. 15: a cross-sectional view of the line with a deformed closing body with detailed representations.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
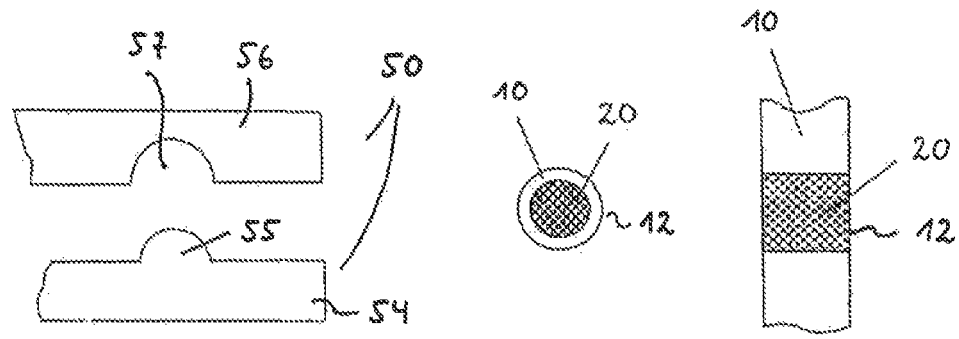
FIGS. 1 to 4: a schematic representation of the steps in the deformation of a closing body by means of a tool in a first embodiment.

FIG. 1, left hand representation, shows a tool 50 which can be actuated manually or by a machine and which has a jaw 54 with a semi-circular projection 55 and a jaw 56 in which a likewise semi-circular recess 57 is arranged, with the diameter of the recess 57 being above that of the projection 55.

FIG. 1, middle representation, shows the line 10 in accordance with the invention in a schematic cross-sectional view, said line being closed by the closing body 20. The closing body 20 is located in that portion 12 of the line 10 which is made flexible. Embodiments are also conceivable in which only that portion 12 is made flexible in which the closing body 20 is located. It is likewise conceivable that the total line 10 is made flexible.

The closing body 20 can be made solid, hollow, open to one side of the line or fully closed. It can comprise porous and impermeable material or also be made hollow and have a filling.

To improve the adhesion between the closing body 20 and the inner side of the wall of the line in the portion 12, provision can be made for adhesive to be arranged between both members, said adhesive having to be metered such that the desired sealing effect is achieved, but the connection nevertheless remains releasable for the case that the passage through the line 10 should be opened.

FIG. 1, right hand representation shows the line 10 in accordance with the invention in a schematic longitudinal sectional view, with the closing body 20 being accommodated in the portion 12 of said line such that it closes the line 10.

Figure 2:
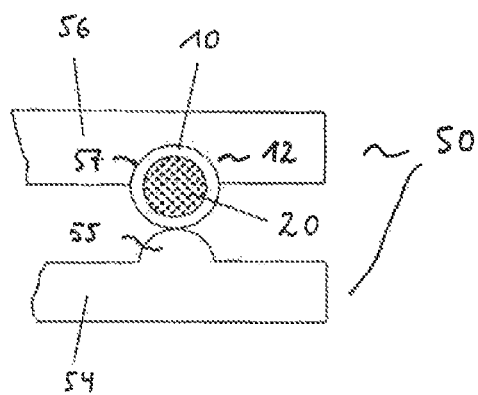

FIG. 2 shows the accommodation of the line 10 in the tool 50. As can be seen from FIG. 2, the radius of the recess 57 of the jaw 56 of the tool 50 approximately corresponds to the outer diameter of the portion 12 of the line 10. The line 10 is fixed in the recess 57 by means of the projection 55, as can be seen from FIG. 2.

Figure 3:
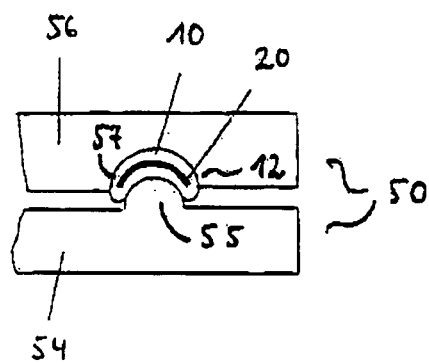

If the tool 50 is actuated by machine or by hand, that is if the jaws 54, 56 are guided together, the line portion between the jaws 54, 56 is squeezed, as is indicated in FIG. 3. The closing body 20 is plastically deformed in this process. Due to the embodiment of the recess 57 and of the projection 55, the shape of part of a circle results for the closing body 20 during deformation, as can be seen from FIG. 3. The force for the deformation of the closing body 20 is transmitted through the wall of the line 10.

Figure 4:
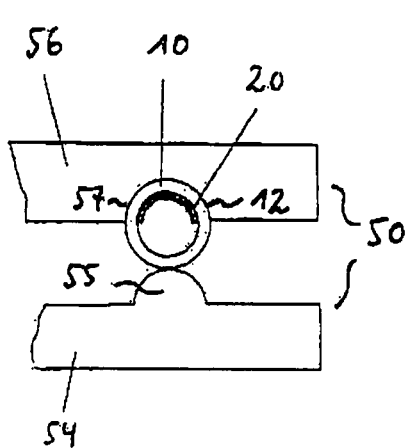

FIG. 4 shows the arrangement after the opening of the tool 50. As can be seen from FIG. 4, the closing body 20 remains in its deformed position and thereby permanently releases a passage through the line 10. The line 10 or its portion 12 again adopts the original design before the deformation process due to the flexible embodiment.

The line 10 or is portion has the same shape before and after the deformation.

Figure 5:
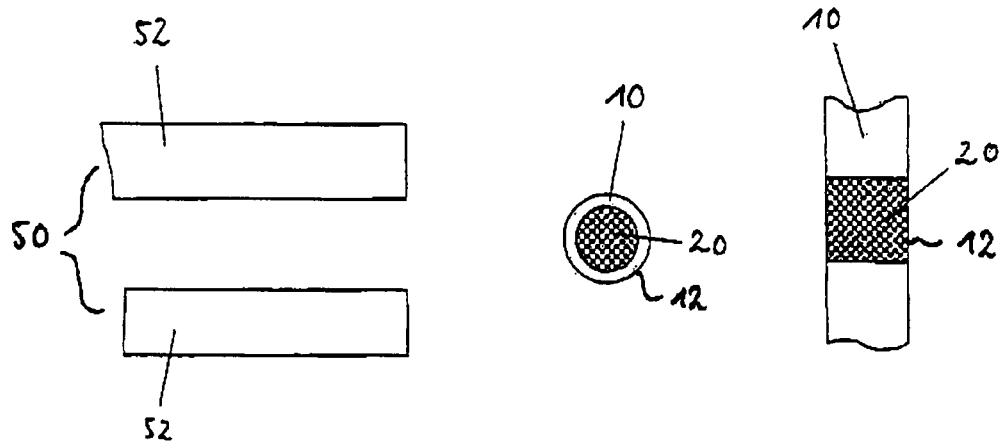
FIGS. 5 to 8: a schematic representation of the steps in the deformation of a closing body by means of a tool in a second embodiment.

FIG. 5 shows a tool 50 with jaws 52 made smooth. The design of the line 10 with a closing body 20 corresponds to the embodiment with respect to FIGS. 1 to 4.

Figure 6:
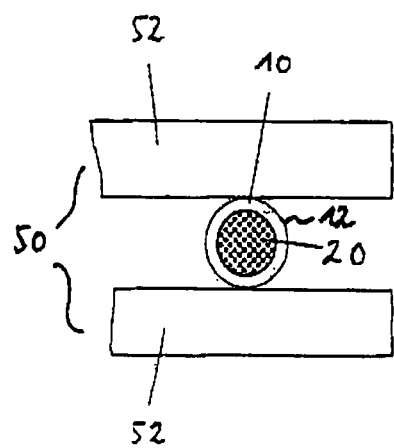

FIG. 6 shows the positioning of the line 10 with a closing body 20 between the jaws 52 of the tool 50.

Figure 7:
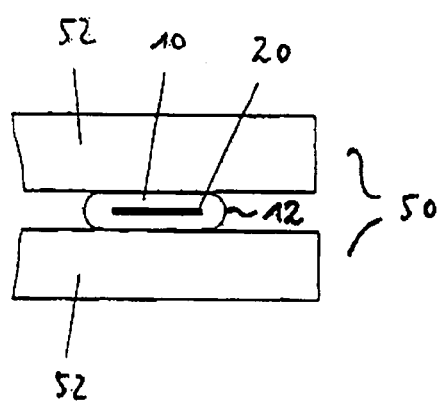

The state is shown in FIG. 7 which results during the compression of the jaws 52 of the tool 50. During compression, the closing body 20 is brought into a shape which holds it in place in the portion 12 of the line 10 after the opening of the tool 50 and nevertheless releases a large passage in the line 10. The force for the deformation of the closing body 20 is transferred through the wall of the line 10 which is flexible at least in the portion 12.

Figure 8:
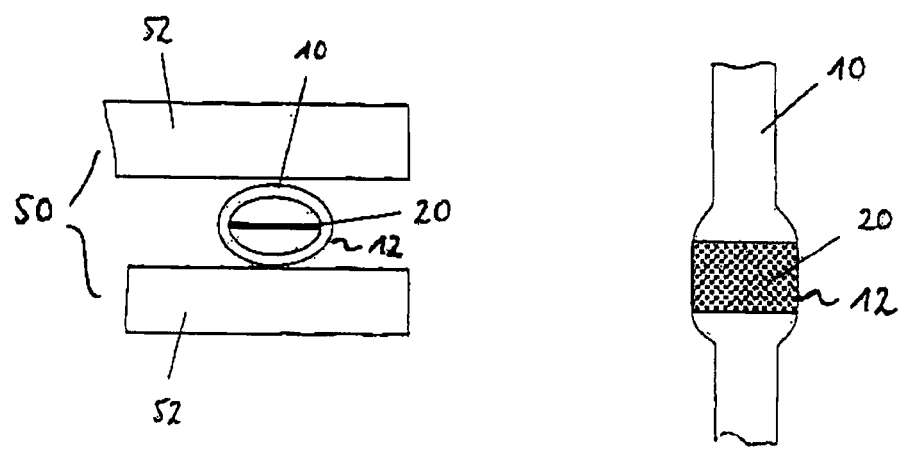

FIG. 8 shows the arrangement after the opening of the tool. As can be seen from FIG. 8, left hand representation, the closing body 20 is permanently deformed and adopts the shape of a strip. The closing body 20 divides the portion 12 of the line 10 into two passage regions above and below the deformed closing body 20. The closing body 20 is permanently located in a shape which fixes it in place after the deformation. For this purpose, as can also be seen from the schematic longitudinal portion in accordance with FIG. 8, right hand representation, the flexible part 12 of the line 10 is extended by the shape of the closing body 20, which results in a restoring force of the portion 12 of the line 10. This force holds the deformed closing body in place in its new shape.

If high demands are made on the pressure resistance of the flexible line, embodiments are possible which permit any desired pressure resistance from a construction aspect. Provision is made for this purpose that the first flexible line is supplemented by a second flexible line which is arranged such that the second flexible line extends at least portionwise inside the first flexible line.

Provision is preferably made in this connection that the first and second lines are connected to one another such that a ring-shaped, peripheral closure arises between both lines. The closing body is located in the interior of the second line. Both lines are preferably made flexible.

Figure 9:
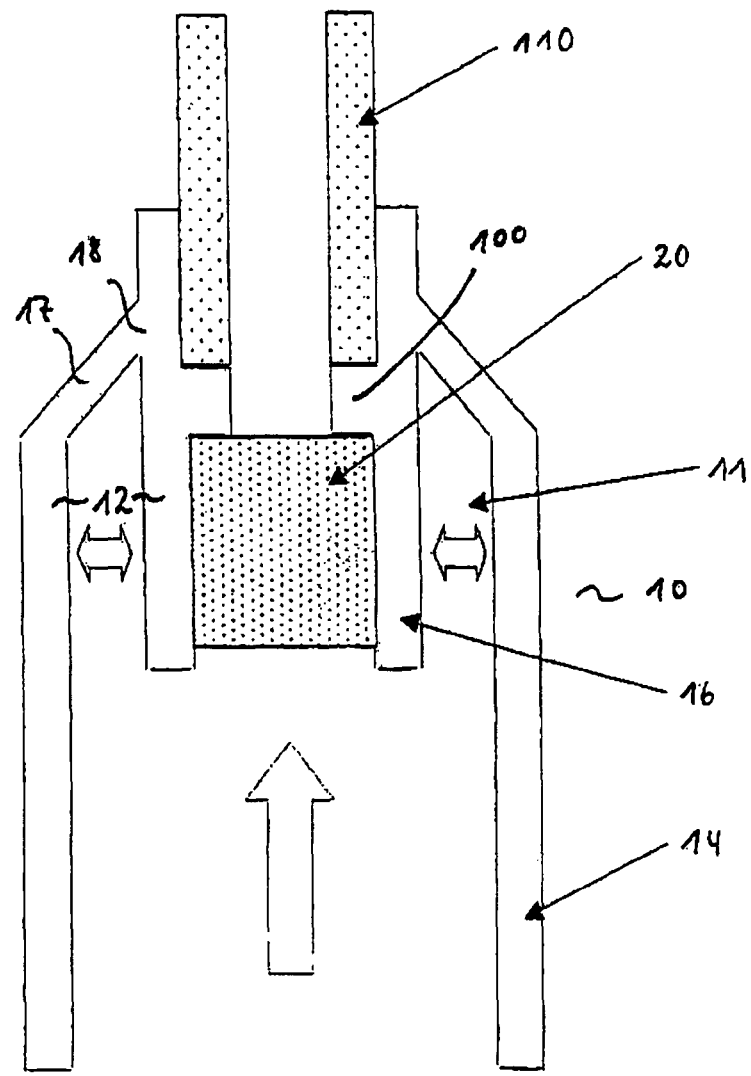
FIG. 9: a schematic representation of a line having a first line part and a second line part in which the closing body is located in an embodiment resistant to pressure on one side.

FIG. 9 shows an embodiment of the invention in this design. The line 10 includes a first line part 14 and a second line part 16, with the closing body 20 being located in the second line part 16 such that it closes it. The second line part 16 has an inwardly projecting web 100 which is contacted by the closing body 20, on the one hand, and by a further line part 110, on the other hand, which represents the connection to further vessels or to the outlet.

As can be seen from FIG. 9, the first line part 14 and the second line part 16 are mutually arranged in that region of the second line part 16 in which the closing body 20 is located such that the first line part 14 concentrically surrounds the second line part 16. A ring-shaped space 11 results in this region between both line parts 14, 16, i.e. both line parts 14, 16 are radially spaced apart from one another in this region. If a pressure acts in the first line part 14, as is indicated by the vertically arranged arrow, this has the result that a force directed to the closing body 20 is exerted onto the portion of the second line part 16 in the space 11 in accordance with the double arrows, whereby an opening of the closure independently of the internal pressure is completely prevented.

The conically tapering region 17 which connects the cylindrical portion of the first line part 14 to the second line part 16 adjoins the cylindrically extending portion of the first line part 14. In the end region of the conical portion 17, the two line parts 14, 16 are connected to one another in a fluid-tight manner while forming the connection point 18.

It is conceivable that the first line part 14 is adjacent to the second line part 16 in the state not acted on by pressure and the position shown in FIG. 9 only results in the state acted on by pressure. An embodiment is furthermore feasible in which a spacing is also formed between both line parts 14, 16 in the state not acted on by pressure while forming the ring space 11.

It can be determined by the positioning of the closing body with respect to the peripheral connection of the first and second line parts 14, 16 whether the pressure resistance is given by one side or by both sides of the closing body 20.

As stated above, the line parts 14, 16 are made flexible at least in the region of the closing body.

Figure 10:
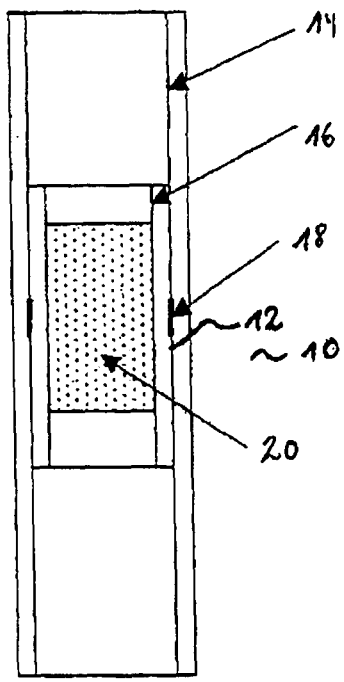
FIG. 10: a schematic representation of the line having a first line part and a second line part in which the closing body is located in an embodiment resistant to pressure on two sides.

FIG. 10 shows an embodiment of the line 10 in accordance with the invention in which the second line part 16 is completely surrounded by the first line part 14, with both line parts 14, 16 contacting one another in the pressure-less state, as is illustrated in FIG. 10. The closing body 20 is sealingly accommodated in the second line part 16. The two line parts 14, 16 are fixedly connected to one another in a fluid-tight manner at the peripheral connection point 18. If the first line part 14 is extended due to the inner pressure prevailing therein, a gap is created between the line parts 14, 16 in which the pressure can propagate such that it presses the second line part 16 onto the closing body 20, whereby a reliable sealing is achieved.

The connection point 18 between the line parts 14, 16 is located approximately centrally at the second line part 16. The closing body 20 is likewise received approximately centrally in the second line part 16 so that an embodiment pressure-tight on two sides results overall.

Figure 11:
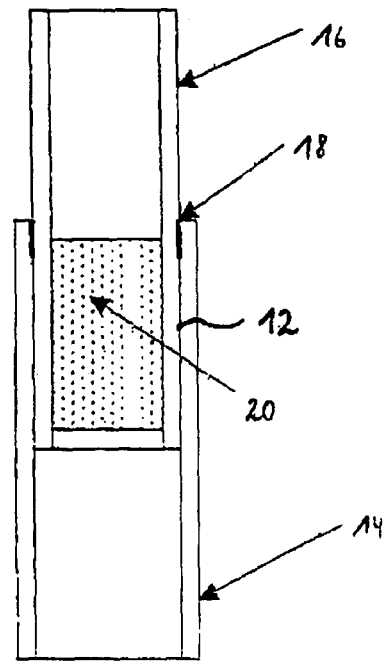
FIG. 11: a schematic representation of the line having a first line part and a second line part in which the closing body is located in a further embodiment resistant to pressure on one side.

FIG. 11 shows an embodiment pressure-tight at one side in which the second line part 16 is partly received inside the first line part 14 and projects beyond it in part. The connection point 18 which connects the line part 14, 16 to one another in a fixed and fluid-tight manner is located in the end region of the first line part 14. The closing body 20 is located in the second line part 16 in that portion in which the second line part 16 is received in the first line part 14. If the first line part 14 is loaded with pressure, this has the result that a gap arises between both line parts 14, 16, with the pressure prevailing in the gap pressing the region of the second line part 16 bounding the gap onto the closing body 20.

Figure 12:
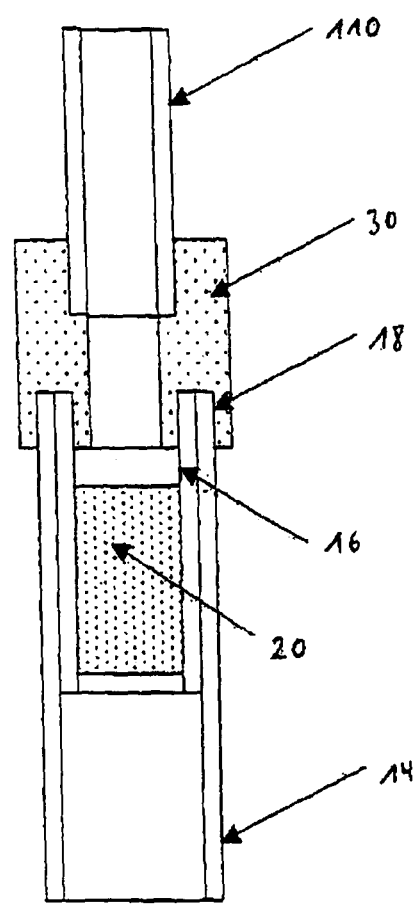
FIG. 12: a schematic representation of the line having a first line part and a second line part in which the closing body is located in a further embodiment pressure tight on one side with an adapter.

FIG. 12 shows a further embodiment of a design pressure-tight on one side in which the line parts 14, 16 terminate flush with one another. An adapter 30 is provided in this end region of the line parts 14, 16 which is placed onto the end regions of the line parts 14, 16 and which presses them to one another in a fluid-tight manner while forming the connection point 18. It is also feasible that the adapter 30 is connected to the line parts 14, 16 by means of adhesive bonding. It also results from this embodiment that, on an application of pressure on the first line part 14, a gap or an annular space results between the two line parts 14, 16, with the pressure prevailing therein pressing the second line part 16 onto the closing body 20.

A line is designated by the reference numeral 110 which extends to further vessels or to an outlet and is in fluid-tight communication with the adapter 30.

FIGS. 13 and 14 show a further embodiment of the present invention in an embodiment pressure-tight on two sides. In this embodiment, the second line part 16 is made in two pieces, with both parts 16', 16" of the second line part 16 bluntly bordering the closing body 20 arranged between them. In this connection, the outer sides of the two parts of the second line part 16 are flush with the outer side of the closing body 20. Furthermore, a first line part 14 is provided which concentrically surrounds the closing body 20 as well as the regions of the parts of the second line part 16 which are adjacent to the closing body 20. The parts of the second line part 16 are connected in a fluid tight manner to the first line part 14 at both sides of the closing body 20.

If the arrangement in accordance with FIG. 13 is acted on by pressure, as is indicated in FIG. 14 by the vertically arranged arrow 140, this has the result that the pressure-carrying medium flows between the end face of a part 16" of the second line part 16 and of the adjoining end face of the closing body 20 and results in a bulging of the first line part 14, as can be seen from FIG. 14. An arched annular space thereby results between the outer side of the closing body 20 and the inner side of the adjacent line part 14. The bulging (arrows 160) of the first line part 14 caused by the exertion of pressure in the region in which the closing body 20 is located has the result that both parts 16', 16" of the second line part 16 experience the force indicated by the arrows 150 in the direction of the closing body 20, which has the result that the end faces of the parts of the second line part 16 are pressed onto the adjoining end faces of the closing body 20 and ensure the sealing.

FIG. 15, top, shows a cross-sectional view of the line 10 in accordance with the invention with the deformed closing body 20 accepted therein. As can be seen from FIG. 15, top, the deformed closing body 20 releases a substantial part of the line cross-section.

As is stated above, the closing body 20 can comprise a plastic material or also a resilient material. Combinations of elastic and plastic materials can also be used.

If the closing body 20 is resilient or flexible, it must be ensured that it does not again adopt its original shape closing the line 10 after its deformation. Any desired means which hold the flexible closing body 20 in its deformed position are conceivable for this purpose.

The illustrations in accordance with FIG. 15, middle and bottom representations, are detailed representations of the detail A in FIG. 15, top, which disclose two different alternatives how the flexible closing body 20 can be held in the deformed position.

FIG. 15, middle illustration, shows the two walls of the closing body 20 which are each provided with an adhesive layer 70. If these adhesive layers 70 are guided toward one another, as is the case with the deformation of the closing body 20 and as is shown in FIG. 15, middle illustration, this has the result that the closing body 20 is fixed in its deformed position shown in FIG. 15. FIG. 15, bottom illustration, shows an alternative embodiment in which the inner sides of the walls of the closing body 20 are provided with a hook and loop fastener 80 which likewise has the effect that the deformed closing body 20 remains in its deformed position.

In the embodiment shown in FIG. 15, the closing body 20 is made, for example, as a hollow body open at one side whose inner walls are provided with the adhesive layer 70 or with the hook and loop fastener 80.

Other means than those shown can naturally also be used to ensure that the closing body 20 remains in its deformed position.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A line of a blood tubing system or of a blood bag system having a line passage, comprising a closing member formed by a plastically deformable closing body which is arranged in the line passage and which closes the line passage in a first state and, when plastically deformed into a second state in which the closing body has a deformed shape different from a shape of said closing body in the first state, opens the line passage, said closing body, once plastically deformed, being fixed in said second state so that said passage remains at least partly open thereafter and said closing body in said second state can no longer be used to close said passage; and at least a portion of the line in which the closing body is located being flexible.

2. The line in accordance with claim 1, wherein the closing body is made solid, porous or as a hollow body which is made open to one or more sides or is made closed.

3. The line in accordance with claim 1, wherein the closing body is made as a hollow body in which a filling is located.

4. The line in accordance with claim 1, wherein the closing body as well as said portion of the line in which the closing body is located are made of materials or comprise materials which adhere to one another.

5. The line in accordance with claim 1, wherein adhesive is located between the closing body and said portion of the line in which the closing body is located to improve adhesion therebetween.

6. The line in accordance with claim 1, wherein a surface of the closing body and/or of an inwardly located surface of the portion of the line in which the closing body is located are made porous or rough.

7. The line in accordance with claim 1, wherein the line has a first line part and a second line part which are in fluid-tight communication with one another at least at one connection point, with the closing body closing the second line part in at least one state and with the first and second line parts being arranged at least portion-wise in a region of the second line part in which the closing body is located such that the first line part surrounds the second line part and both line parts are spaced apart from one another or can be released from one another at least portion-wise in said region.

8. The line in accordance with claim 7, wherein the first and the second line parts are arranged concentrically to one another.

9. The line in accordance with claim 7, wherein both line parts are spaced apart from one another in that portion of the second line part in which the closing body is arranged; and wherein both line parts are connected to one another by means of a connection portion.

10. The line in accordance with claim 9, wherein said connection portion tapers conically.

11. The line in accordance with claim 7, wherein the second line part is received in the first line part; and wherein the connection point is arranged in the marginal region of the second line part or spaced apart therefrom.

12. The line in accordance with claim 11, wherein the connection point is arranged centrally at the second line part.

13. The line in accordance with claim 7, wherein the second line part is arranged partly in the first line part and partly projects beyond it; and wherein the connection point is arranged in the end region of the first line part.

14. The line in accordance with claim 7, wherein an adapter is provided which is placed onto the first and second line parts.

15. The line in accordance with claim 1, wherein a first line part and a second line part are provided, with the second line part being made in two parts and each of the two second line parts adjoining the closing body bluntly, with the first line part surrounding the second line part and being in fluid-tight communication with the two second line parts at both sides of the closing body.

16. The line in accordance with claim 1, wherein the closing body includes one or more resilient and/or plastic materials.

17. The line in accordance with claim 1, wherein the closing body is resilient; and wherein means are provided which fix the closing body in a deformed position.

18. A method of opening a line in a blood tubing system or of a blood bag system using a closing member formed by a plastically deformable closing body arranged inside the line, said method including plastically deforming the closing body from a first state in which it closes the line for the purpose of opening the line such that a passage through the line is released, said step of plastically deforming acting to change said closing body into a second state having a deformed shape different from a shape of said closing body in said first state, said closing body, once plastically deformed, being fixed in said second state so that said passage remains at least partly open thereafter and said closing body in said second state can no longer be used to close said passage.

19. The method in accordance with claim 18, wherein the deformation of the closing body is carried out using a tool.

20. The method in accordance with claim 19, wherein the tool is represented by hand-actuated pincers or is a component of a machine.

21. The method in accordance with claim 19, wherein the tool has smooth jaws.

22. The method in accordance with claim 19, wherein the tool has a jaw with a projection and a jaw with a recess in which the projection at least partly engages with a closed tool.

23. The method in accordance with claim 18, wherein the deformation of the closing body takes place such that said closing body is fixed against displacement in the line after its deformation.

24. A blood tube or a blood bag having a line and a closing member formed by a plastically deformable closing body which is arranged within a flexible portion of said line, said closing body closing a passage in the line when in a first state and, when plastically deformed into a second state in which the closing body has a deformed shape different from a shape of said closing body in the first state, said closing body opening the line passage, said closing body, once plastically deformed, being fixed in said second state so that said passage remains at least partly open thereafter and said closing body in said second state can no longer be used to close said passage.

* * * * *